United States Patent [19]
Klothen

[11] Patent Number: 4,764,511
[45] Date of Patent: Aug. 16, 1988

[54] LARVICIDAL COMPOSITIONS EMPLOYING DIFLUBENZURON

[75] Inventor: Irving Klothen, Princeton, N.J.

[73] Assignee: American Cyanamid Company, Stamford, Conn.

[21] Appl. No.: 853,442

[22] Filed: Apr. 23, 1986

Related U.S. Application Data

[63] Continuation-in-part of Ser. No. 731,578, May 9, 1985, abandoned.

[51] Int. Cl.$^4$ .............................................. A01N 47/28
[52] U.S. Cl. ..................................................... 514/594
[58] Field of Search ......................................... 514/594

[56] References Cited

U.S. PATENT DOCUMENTS

| | | | |
|---|---|---|---|
| 3,966,958 | 6/1976 | Baile et al. | 514/594 |
| 4,166,107 | 8/1979 | Miller et al. | 424/22 |

FOREIGN PATENT DOCUMENTS

| | | | |
|---|---|---|---|
| 57-2258 | 1/1982 | Japan | 514/594 |
| 57-67505 | 4/1982 | Japan | 514/594 |

Primary Examiner—Allen J. Robinson
Attorney, Agent, or Firm—Estelle J. Tsevdos

[57] ABSTRACT

The present invention relates to novel compacted granular larvicidal feed premix compositions of N[[(4-chlorophenyl)amino]carbonyl]-2,6-difluorobenzamide, a method for their preparation and an improved method for the control of larvae utilizing these compositions.

8 Claims, No Drawings

LARVICIDAL COMPOSITIONS EMPLOYING DIFLUBENZURON

The present application is a continuation-in-part application of pending parent application for U.S. Letter Patent, Ser. No. 731,578, filed May 9, 1985, now abandoned.

BACKGROUND OF THE INVENTION

The control of fly larval infestation is important in agricultural in order to avoid the illnesses and economic losses associated with such insect pest infestation. A method of controlling fly larval by direct application to the larval breeding medium is widely known in the industry. The method involves such direct utilization of the compound, N[[4-chlorophenyl)amino]carbonyl]-2,6-difluorobenzamide, sold under the tradename of DIMILIN ® insecticide, a registered trademark of Duphar BV of Amsterdam, Holland (hereinafter referred to as diflubenzuron, the generally recognized generic chemical name).

Due to the effectiveness of diflubenzuron when used against fly larvae, the search for a more beneficial manner to control such fly larvae has spurred and continues to spur new research efforts. One attractive method for fly larvae control is to utilize diflubenzuron in feeds for controlling fly larvae in excreted feces. This method is commonly referred to as feed-through application. For instance diflubenzuron at levels of 0.5 to 1.0 mg/kg animal body weight, has been mixed directly into the feed of calves and dairy cattle and has shown effective control of house fly and face fly larval in the feces (R. W. Baker et al, *J. Georgia Entomol. Soc.*, 11 (1976) 1: 67–71 and R. W. Miller, *J. Economic Entomol.* 67 (1974) 5: 697).

In addition to this direct feed addition method, diflubenzuron has been encapsulated and tested for insecticidal activity, F. W. Knapp et al., Symp. Int. Meeting Controlled Release Soc. (Academic Press, 1980), as well as being applied in mineral blocks and delivered in a sustained-release bolus form (U.S. Pat. No. 4,166,107, issued to J. A. Miller et al on AUg. 28, 1979).

SUMMARY OF THE INVENTION

The present invention relates to novel compacted granular feed premix compositions containing diflubenzuron. These granular feed premix compositions provide enhanced larvicidal effectiveness and fly control of surprisingly low doses of diflubenzuron.

It is an object of the present invention therefore to provide novel such compacted granular feed premix compositions with improved larvicidal effectivness and fly control.

It also is an object of the present invention to provide a method for preparing the novel compacted granular feed premix compositions of the invention.

These and further objects of the present invention will become more apparent by the more detailed description of the invention provided herein.

DETAILED DESCRIPTION OF THE INVENTION

The present invention relates to compacted granular feed premix compositions comprising, on a weight basis, about 0.5% to 84.0% diflubenzuron; about 0% to 10% whole dried whey; about 0% to 2% water and the remainder of a compactable, insoluble carrier to total the composition of 100%.

Compactable, insoluble carriers suitable for use in the compositions of the present invention include clays and mineral salts, such as $CaSO_4$, $BaSO_4$ or other mineral salts, $CaCl_2$. The preferred carrier, however, is $CaSO_4$ dihydrate. Preferred compacted granular premix compositions of this invention have a granular particle size of 10 mesh to 100 mesh, with a particle size range of 20 mesh to 60 mesh being preferred.

This invention also relates to methods for the preparation of these compacted granular compositions. It unexpectedly has been discovered that compositions of the present invention, prepared by the compaction and granulation process of the invention, provide compositions which provide effective control of larvae when administering doses in animal feeds of diflubenzuron at rates as low as 0.025 mg/kg of animal body weight. Surprisingly, the compacted granulated compositions of the invention are more efficacious than diflubenzuron alone, the uncompacted composition or an alfalfa feed premix of diflubenzuron administered in animal feed for the feed through control of fly larvae and resulting fly control (see Table I). This invention also provides an improved method for controlling fly larvae and flies in the feces of animals. This is accomplished by orally administering, in an animal feedstuff or feed supplement, sufficient quantities of the present compositions to provide about 0.025 mg/kg to 10 mg/kg per animal per day of diflubenzuron.

TABLE I

| % Fly control obtained by various feed through compositions | | |
|---|---|---|
| Day | Diflubenzuron 0.5 mg/kg/day a.i. | 4.0% Alfalfa premix 0.5 mg/kg/day a.i. | 4.0% Compacted granular $CaSO_4$ premix 0.5 mg/kg/day a.i. |
| 7 | 64.5 | 44.0 | 85.6 |
| 14 | 84.5 | 69.5 | 97.0 |
| 21 | 76.5 | 97.5 | 100.0 |

The compositions of the invention may be administered by addition to animal feeds, protein concentrates or supplements and other feed ingredient compositions such as vitamin or mineral supplements.

The feed premix compositions of the present invention may readily be prepared by compacting a mixture of the compactable carrier and diflubenzuron. Alternatively, an appropriate amount of water may be sprayed onto the carrier and mixed until homogeneous, and then diflubenzuron is added, mixed with the homogeneous mixture and the resulting blend compacted on serrated compaction rolls. The compacted blend is then ground to the desired particle size range of about 10 to 100 mesh, with a preferred range of 20 to 60 mesh. This is then packaged.

Material of smaller particle size is recycled through the compaction procedure and reground in order to obtain the optimum particle size, while larger particles also may be recycled or merely reground.

The compositions of the invention are further illustrated by the following non-limiting examples.

EXAMPLE 1

Preparation of compacted granular larvicidal premix compositions

Water (200 g) is sprayed into $CaSO_4$ (9.335 kg) while blending the mixture. After ten minutes, diflubenzuron (465 g,) is added, and blending is continued until the mixture is homogeneous. A portion of this mixture (5.0 kg) is compacted using 2" compaction rolls, with a roll speed of 5.5, a feeder speed of 1.5 and pressure of 1500 psig.

TABLE II

|   | Treatment | Rate mg/kg | Average % pupae recovered* | | | | Average % fly control* | | |
|---|---|---|---|---|---|---|---|---|---|
|   |   |   | Day 0 | Day 4 | Day 7 | Day 14 | Day 4 | Day 7 | Day 14 |
| A | Controls | None | 91 | 93 | 87 | 83 | — | — | — |
| B |   | 0.05 | 87 | 43 | 46 | 51 | 97 | 97 | 95 |
| C |   | 0.10 | 83 | 30 | 10 | 17 | 99 | 100 | 100 |
| D |   | 0.25 | 86 | 9 | 1 | 2 | 100 | 100 | 100 |
| E |   | 0.50 | 92 | 4 | 1 | 2 | 100 | 99 | 100 |
| F | Diflubenzuron | 0.10 | 92 | 93 | 73 | 61 | 95 | 82 | 89 |
| G | Diflubenzuron + CaSO₄ not as compacted granular premix | 0.10 | 83 | 78 | 35 | 57 | 88 | 97 | 83 |

*Average of three animals per group and two samples per animal.

The resulting compacted material is ground, and the ground material classified on a shaker equipped with two sieves (20 and 60 mesh), to give the desired compacted granular premix composition. Material less than 60 mesh is blended with 2.5 kg of the remaining mixture, and the compaction, grinding and classification steps repeated. This is continued through three cycles or until greater than 90% of the original mixture is converted to the preferred particle size. Material greater than 20 mesh is ground and classified directly into the preferred size range.

EXAMPLE 2

Efficacy of compacted granular larvicidal feed premix compositions

Twenty-one Hereford steers weighing approximately 250 to 450 kg each are provided with 1.0 kg of dairy concentrate daily plus free choice silage and water ad libitum. Each steer individually housed is acclimatized to these conditions and observed until all animals are consuming the silage-concentrate mixture and their manure appears normal.

Then the compacted granular feed premix is added to the daily ration of concentrate and fed daily for 14 days at the different rates indicated in Table II. Two manure samples (200 g) are collected from each animal on days 0, 4, 7 and 14 after treatment commences. Each sample is seeded with 25 WHO strain house fly first instar larvae and the number of pupae and emerged adult flies are recorded.

The results of these experiments, which are summarized in Table II below, demonstrate the improved efficacy of the compacted granular premix compositions of the invention compared to diflubenzuron alone and a diflubenzuron and CaSO₄ mixture which has not been compacted and granulated.

EXAMPLE 3

Water (200 g) is sprayed onto CaSO₄ (5.67 kg) while blending the mixture. After ten minutes diflubenzuron (4.122 kg) is added and the blending continued until the mixture is homogeneous. One-half of this mixture (5.0 kg) is compacted using a two inch compaction rolls, with a roll speed of 5.5, a feeder speed of 1.5 and pressure of 1500 psig.

The resulting compacted material is ground and classified in a shaker equipped with two sieves (20 and 60 mesh), to the desired particle size. Material less than 60 mesh is blended with 2.5 kg (one-half of remaining) mixture and compacted/ground/classified. This is continued through three cycles or until greater than 90% of the original mixture is converted to the preferred particle size. Material greater than 20 mesh is ground and classified directly into the preferred particle size range.

EXAMPLE 4

Diflubenzuron (12.6 g) is blended with 9.874 kg CaSO₄ and mixed. One-half of this uncompacted blend (5.0 kg) is compacted using a two inch compaction rolls, with a roll speed of 5.0, a feeder speed of 2.5 and a pressure of 1500 psig.

The resulting compacted material is ground and classified on a shaker equipped with screens ranging from 12 to 60 mesh. Material less than 60 mesh is blended with 2.5 kg (one-half of remaining) original blend and the compaction/grinding/classification cycle repeated. This sequence is continued for at least three cycles or until greater than 90% of the original blend is converted to the desired particle size range. Material greater than 12 mesh is ground/classified directly into the preferred particle size range.

EXAMPLE 5

Water (200 g) is blended with 9.335 kg CaCl₂ and mixed. To this mixture, 465 g of diflubenzuron is added, and blending is continued until the mixture is homogeneous. A portion of this uncompacted blend (5.0 kg) is compacted using two inch compaction rolls, with a roll speed of one roll speed 7.0 and pressure of 1000 psig.

The resulting compacted material is ground and classified as described in Example 4. Again at least three cycles of blending/compaction/grinding and classification are used.

EXAMPLES 6-8

Compositions which have been or can be prepared in accordance with the present invention are listed below. The components are thoroughly blended, and this blended composition is transferred to a holding bin that feeds a set of serrated rolls (e.g. Fitzpatrick chillsonator). The composition is fed to the rolls and compacted into a ribbon of materials. Thereafter, it is granulated and sieved for size, with the procedure repeated, if necessary, to obtain the appropriate mesh sizes.

| | PREMIX COMPOSITIONS | | |
|---|---|---|---|
| | % (w/w) | | |
| Components | Example 6 | Example 7 | Example 8 |
| diflubenzuron (95–100% technical) | 41.2 | 55.5 | 83.33 |
| whey | 2.0 | 4.5 | 8.0 |
| water | 1.5 | 0.5 | 0.0 |

-continued

| PREMIX COMPOSITIONS | | | |
|---|---|---|---|
| | % (w/w) | | |
| Components | Example 6 | Example 7 | Example 8 |
| CaSO$_4$ dihydrate | 55.3 | 39.0 | 8.67 |

What is claimed is:

1. A compacted granular larvicidal feed premix composition for animal feedstuff or a feed supplement comprising, on a weight basis: about 0.5% to 84.0% diflubenzuron; about 0% to 10% whole dried whey; about 0% to 2% water; and the remainder a compactible, insoluble carrier to total said composition to 100%; wherein said carrier is CaSO$_4$ dihydrate and wherein said composition is compacted.

2. A composition according to claim 1, wherein said composition has a particle size of 10 mesh to 100 mesh.

3. A composition according to claim 2, comprising on a weight basis: about 0.5% to 10.0% diflubenzuron; 87% to 98.5% CaSO$_4$ dihydrate; and 1.0% to 2.0% water.

4. A composition according to claim 3, wherein said composition has a particle size of 20 mesh to 60 mesh.

5. A method for controlling flies and fly larvae in the feces of animals, comprising: administering to said animals a compacted granular feed premix containing, on a weight basis, about 0.5% to 84.0% diflubenzuron; about 0% to 10% whole dried whey; about 0% to 2% water; and the remainder CaSO$_4$ dihydrate to total said composition to 100%; and wherein said method provides about 0.025 mg/kg to 1.0 mg/kg per animal per day of diflubenzuron.

6. A method according to claim 5, wherein said compacted granular feed premix composition has a particle size of 10 mesh to 100 mesh.

7. A method according to claim 6, wherein said compacted granular feed premix composition comprises, on a weight basis: about 0.5% to 10.0% diflubenzuron; 87.0% to 98.5% CaSO$_4$ dihydrate; and 1.0% to 2.0% water.

8. A method according to claim 7, wherein said composition has a particle size of 20 mesh to 60 mesh.

* * * * *